US00PP12637P2

(12) United States Plant Patent
Probst

(10) Patent No.: US PP12,637 P2
(45) Date of Patent: May 21, 2002

(54) PHYSOSTEGIA PLANT NAMED 'MISS MANNERS'

(75) Inventor: Darrell R. Probst, 63 Williamsville Rd., Hubbardston, MA (US) 01452-1315

(73) Assignee: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 09/607,428

(22) Filed: Jun. 27, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para

(57) ABSTRACT

A new cultivar of *Physostegio virginiana* named 'Miss Manners' characterized by its clump-forming nature, compact, sturdy growth habit and profuse white flowers that bloom over a long period.

4 Drawing Sheets

BACKGROUND OF THE INVENTION

The invention presents a new and distinct cultivar of *Physostegia virginiana* and will be referred to hereafter by the cultivar name 'Miss Manners'. 'Miss Manners' is a new hardy Obedient Plant, a perennial herb grown for landscape use.

The new cultivar was discovered by the inventor in his nursery in Hubbardston, Mass. in 1988 in a mixed population of open pollinated seedlings derived from *Physostegia virginiana* 'Rosea'. 'Miss Manners', was selected as unique for its clump-forming growth habit, its compact, sturdy growth, its ability to remain upright in bloom and for its long season of bloom. The new cultivar can be readily distinguished from all other cultivars of *Physostegia virginiana* by the characteristics that are described hereafter.

'Miss Manners' differs from its parent plant *Physostegia virginiana* 'Rosea' (unpatented) in that 'Rosea' has a taller, non clump-forming habit of growth and rose-pink blossoms. The closest comparative is *Physostegia virginiana* 'Summer Snow' (unpatented) with a similar white flower color. Although reported to spread less rampantly than the species, 'Summer Snow' has a vigorous, spreading growth habit, tends to flop when in bloom and is generally 6" taller as compared to 'Miss Manners' (Table 1).

The first asexual propagation was done by division, by the inventor in September of 1991 in Hubbardston, Mass. Subsequent asexual propagation of the new cultivar has been accomplished by division, stem cuttings and tissue culture. The characteristics of this cultivar have been determined to be stable and reproduce true to type in successive generations.

SUMMARY OF THE INVENTION

The following traits have been repeatedly observed and are determined to be the characteristics of the new cultivar. The combination of these traits distinguish the cultivar from all others in commerce.

1. 'Miss Manners' has a clump-forming growth habit which is unique and unlike any other Obedient Plant in the trade. Its rhizomes are very short, so it does not spread rapidly as do other known cultivars.

2. The plant habit is compact. 'Miss Manners' is generally 6" shorter than 'Summer Snow'.

3. The pure white flowers of 'Miss Manners' are borne in profusion and rebloom occurs over a long time period from axillary buds which regularly form down the length of the flowering stem. Secondary axillary bloom spikes form at the leaf nodes of the primary axillary spikes, producing a concentration of bloom. The axillary bloom spikes of 'Summer Snow' do not regularly form secondary axillary bloom spikes from their leaf axils, resulting in a narrower, less floriferous bloom spike.

4. The sturdy stems remain erect and do not tend to flop while in bloom.

BRIEF DESCRIPTION OF THE DRAWING

The plants depicted in these photographs were set out originally as five individual stems in the fall of 1998 in Hubbardston, Mass. The photograph on Sheet 1 was taken on Jul. 18, 1999. The photograph on Sheet 4 was taken on Jul. 8, 1999. The root photographs (Sheets 2, 3) were taken in Nov. 1999.

Sheet one: the entire plant is shown to depict the plant habit of 'Miss Manners'.

Sheet two: depicts the root system of 'Miss Manners' (left) next to that of 'Summer Snow' (right) to demonstrate the difference in rhizome length.

Sheet three: depicts one year's worth of growth on rhizomes of 'Miss Manners' (right) with short internodes as compared to rhizomes of 'Summer Snow' (left) showing much longer internodes.

Sheet four: depicts the cultivar 'Miss Manners' (right) next to the cultivar 'Summer Snow' (left) where the difference in height and growth habit can be readily observed. 'Miss Manners' has sturdy upright growth, while the stems of 'Summer Snow' have fallen away from the center of the plant and turned upward.

The color is as acurate as possible by conventional photography.

BOTANICAL DESCRIPTION OF THE PLANT

The following is a detailed description of the new cultivar as on 2-year old plants grown in the ground in the inventor's nursery in Hubbardston, Mass. Phenotypic differences may be observed with variations in environmental, climatic and cultural conditions. The color determination is in accordance with The R.H.S. Colour Chart of The Royal Horticultural Society, London, England, except where general color terms of ordinary dictionary significance are used.

Botanical classification: 'Miss Manners' is a cultivar of *Physostegia virginiana.*

Family: Lamiaceae.

Commercial classification: Obedient Plant, False Dragonhead.

Garden use: An herb that is treated as a perennial landscape plant.

Parentage: Naturally occuring seedling of *Physostegia virginiana* 'Rosea' discovered in a nursery bed.

Plant description:

*Blooming period.*—Early July to late August.

*Blooming habit.*—Terminal and axillary spikes.

*Type.*—Rhizomatous perennial herb.

*Culture.*—Sunny location in well-drained, moderately fertile soils.

*Plant habit.*—Compact, clump-forming, sturdy, with erect straight stems.

*Propagation.*—Stem cuttings, division, tissue culture.

*Root system.*—Rhizomatous.

*Size.*—2-year old plants grown in a nursery bed are 65–72 cm in height, 27–36 cm in width.

Flower:

*Type.*—Zygomorphic, sympetalous, bilabiate, perfect flowers.

*Arrangement.*—2 ranked, flowers closely held on terminal and axillary spikes. 28–56 flowers on terminal spikes, 18–32 flowers on axillary spikes.

*Calyx.*—5 sepals fused to ¾ of their length, Tubular campanulate, with sharp-tipped, short triangular teeth. Color: Medium green, 144A. Length: Sepals 6–8 mm, teeth 1–1.5 mm in length.

*Corolla.*—5 petals 2–3 cm long, fused along ¾ of their length, limb 2-lipped, upper lip erect and concave, nearly entire, lower lip 3-lobed and recurved. Color: Pure white, closest to 155D.

*Reproductive organs.*—Stamens—4 didymous, outer pair of stamens 2–3 cm long, equal in length to the upper lip of corolla. Anthers basifixed, 2-celled, 0.75 mm–1 mm in length. Color: Medium brown, 164A. Filaments fused to corolla for ¾ their length. Color: Pure white, closest to 155D. Pistil—1, 2–3 cm long, equal in length to upper lip of corolla. Stigma bifid at apex, minute at stylar branch tips. Color: Pure white, closest to 155D. Style gynobasic. Color: Pure white, closest to 155D. Ovary superior.

Fruit: Four glabrous, 3-angled nutlets.

*Size.*—Nutlets 3–4 mm in length, 1.5–2 mm in width.

*Color.*—Dark brown, 200A.

Stems:

*Shape.*—Square, somewhat succulent.

*Size.*—Main stems 5–8 mm in diameter, secondary stems to 5 mm. diameter.

*Surface.*—Glabrous.

*Color.*—Dark green, 137-B.

Foliage description:

*Shape.*—Narrowly elliptic with lanceolate tendencies.

*Division.*—Simple.

*Base.*—Cuneate.

*Apex.*—Bluntly acute.

*Margins.*—Serrate.

*Attachment.*—Sessile.

*Arrangement.*—Opposite, 2-ranked.

*Attitude.*—Re-curved.

*Surface.*—Glabrous.

*Venation.*—Mid-rib recessed, others not prominent.

*Color.*—Upper surface: Dark green 147-A, Lower surface: Dark green 137-A.

*Size.*—Median leaves: Length: 11–14 cm., Width: 2.5–3.5 cm. Lowermost and uppermost leaves much reduced.

*Internodes.*—4.5–7.5 cm in length.

Weather tolerance: Plants have been hardy to U.S.D.A. Zones 2–9.

Disease and pest resistance: Plants to dates have not been observed to be resistant to pests common to *Physostegia virginiana.*

TABLE 1

| | 'Miss Manners' | 'Summer Snow' |
|---|---|---|
| Rhizome length: | | |
| Range: | 2–4.3 cm | 9–18 cm |
| Average: | 3.2 cm | 12.4 cm |
| Plant Size: | | |
| Height: | 45–75 cm | 75–105 cm |
| Internode length: | 4.5–7.5 cm | 5.5–9.0 cm |

I claim:

1. A new and distinct cultivar of *Physostegia virginia* plant named 'Miss Manners' as illustrated and described.

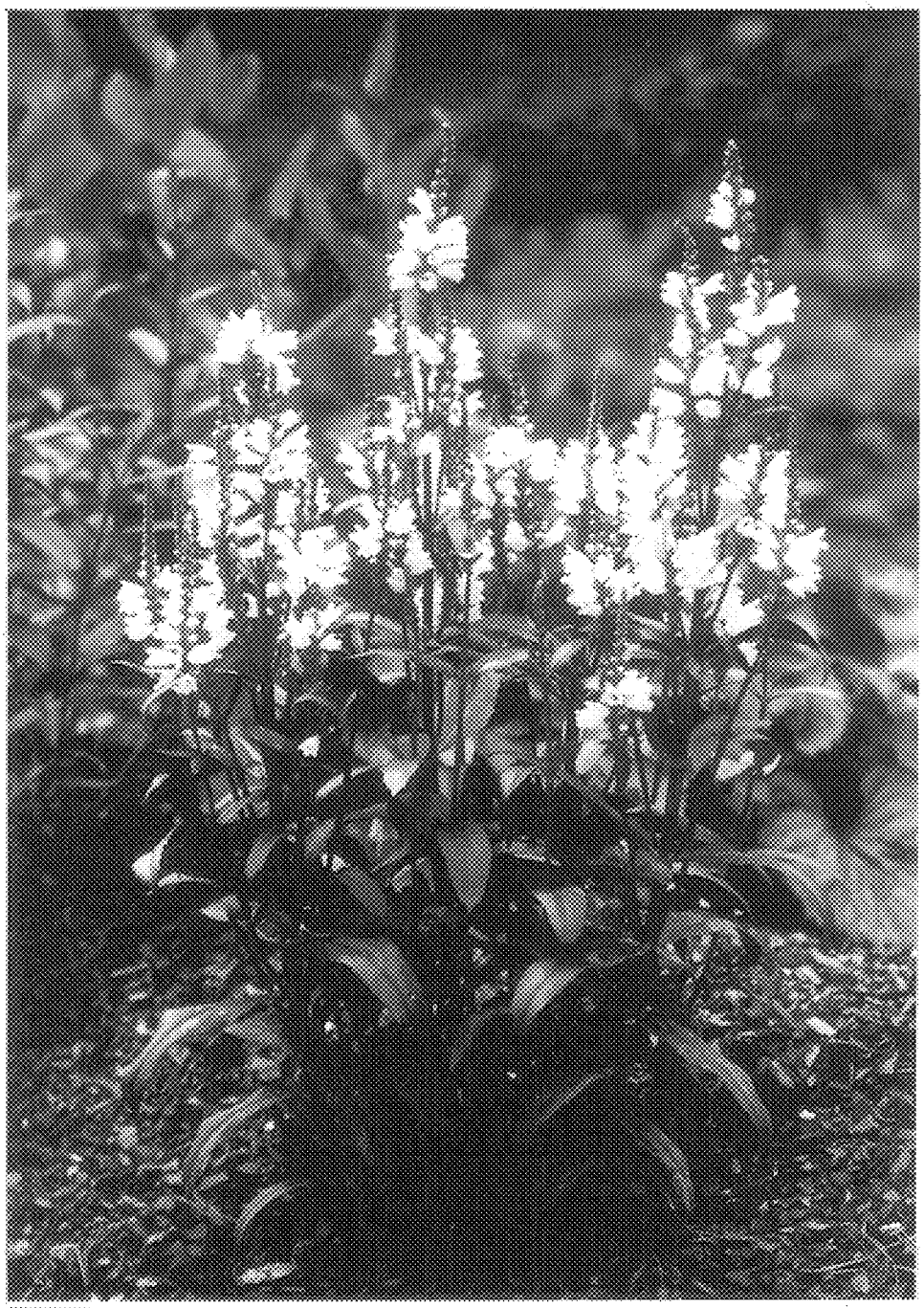

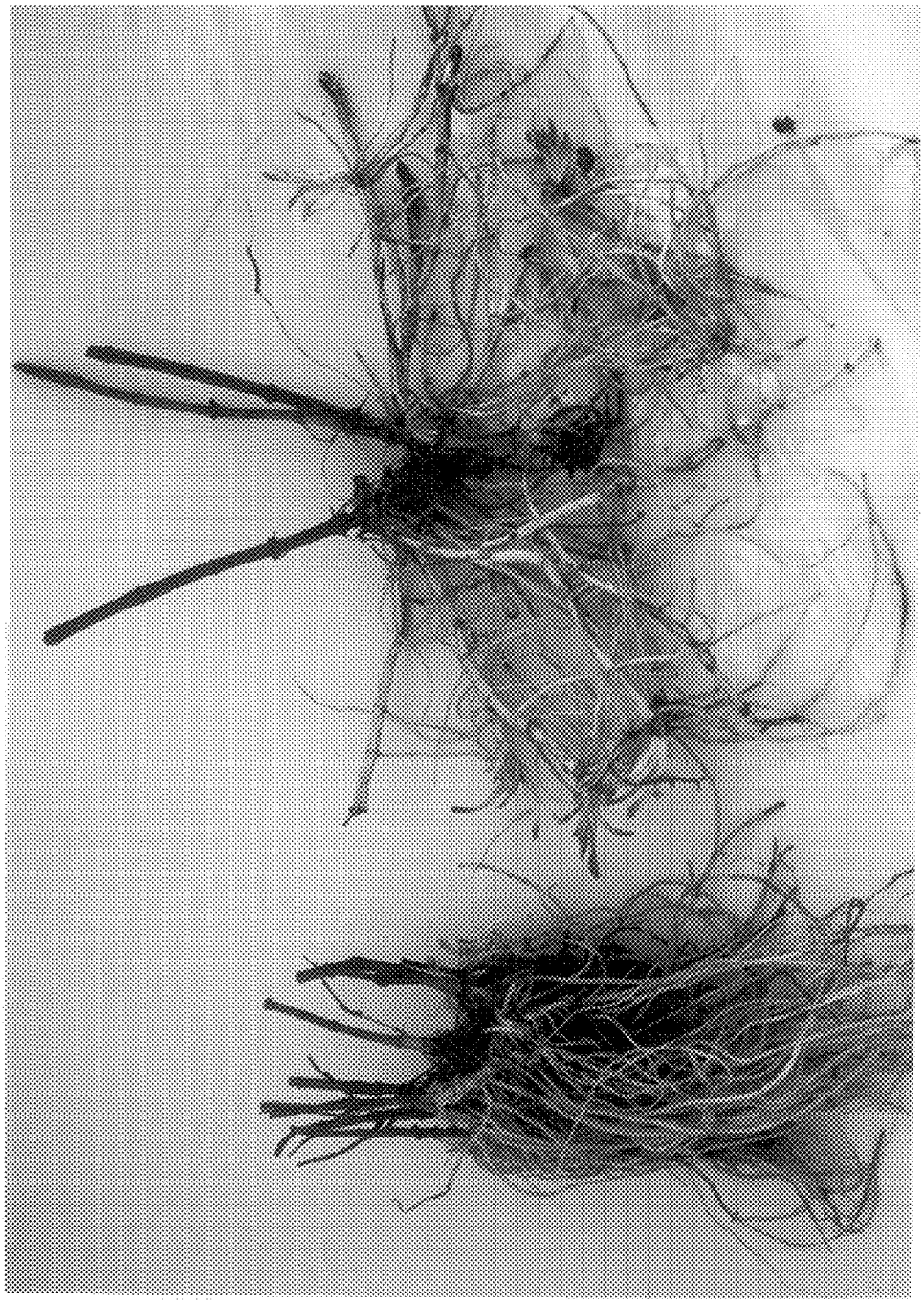

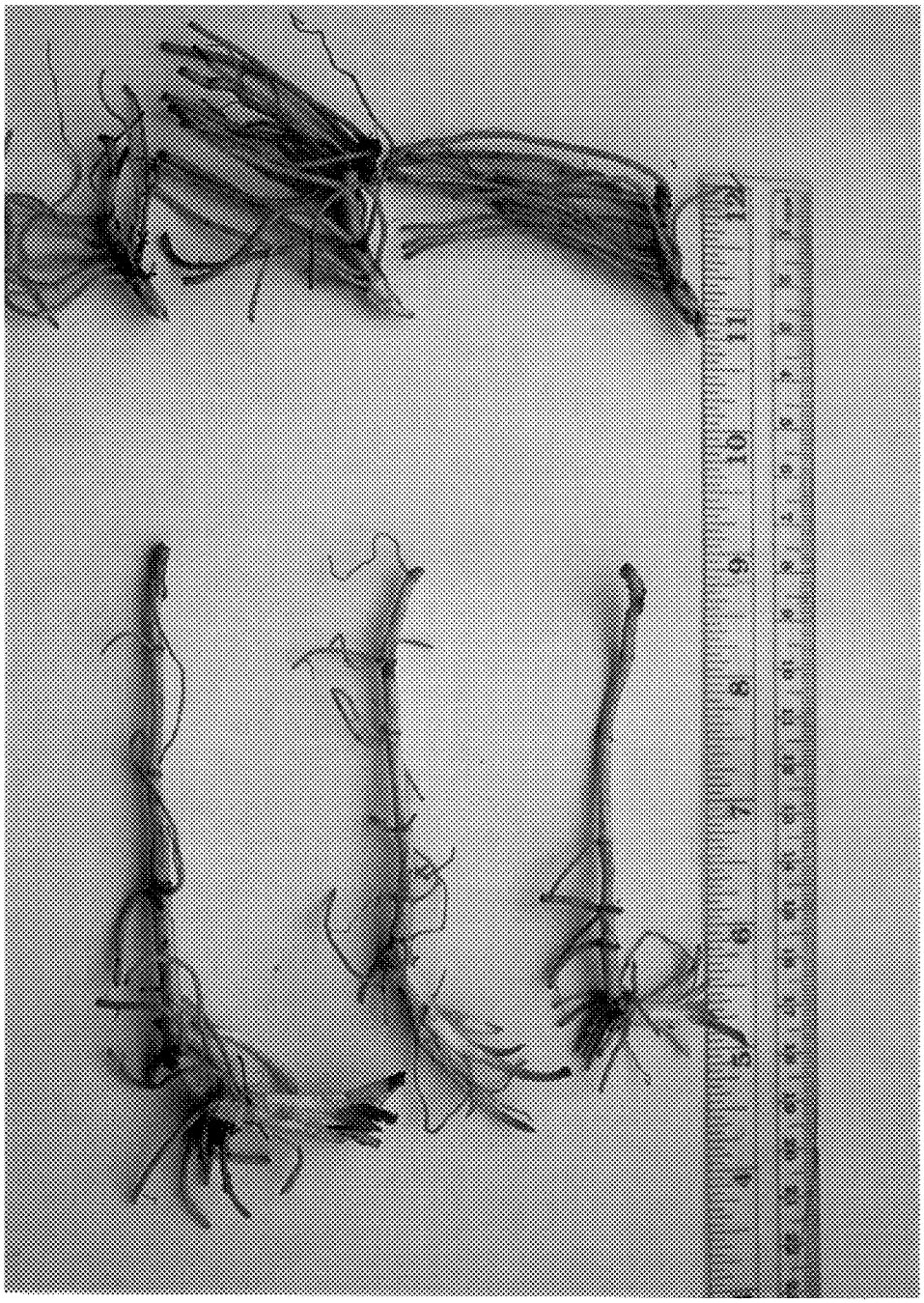

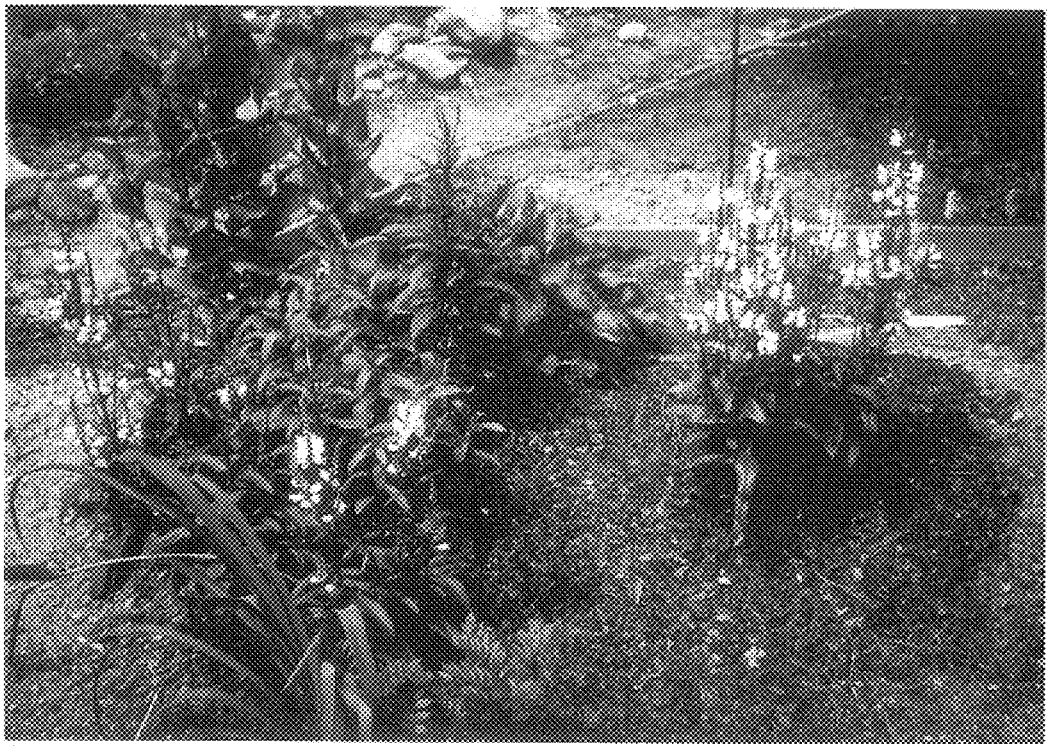

* * * * *